United States Patent [19]
Schmitt et al.

[11] Patent Number: 4,836,212
[45] Date of Patent: Jun. 6, 1989

[54] APPARATUS FOR THE NONINVASIVE DETERMINATION AND ACOUSTICAL REPRESENTATION OF THE DYNAMIC BEHAVIOR OF PERIPHERAL VENOUS HEMODYNAMIC

[75] Inventors: Hans J. Schmitt; Vladimir Blazek, both of Aachen, Fed. Rep. of Germany

[73] Assignee: Fa Nattermann Arzneimittel GmbH, Cologne, Fed. Rep. of Germany

[21] Appl. No.: 26,686

[22] Filed: Mar. 17, 1987

[30] Foreign Application Priority Data

Mar. 18, 1986 [DE] Fed. Rep. of Germany ....... 3609073

[51] Int. Cl.$^4$ ............................................. A61B 5/02
[52] U.S. Cl. ................................... 128/667; 128/672; 128/689
[58] Field of Search ............... 128/633, 634, 664–667, 128/672, 689

[56] References Cited
U.S. PATENT DOCUMENTS

| | | | |
|---|---|---|---|
| 3,658,060 | 4/1972 | Eklof | 128/673 |
| 3,895,316 | 7/1975 | Fein | 128/696 X |
| 4,703,758 | 11/1987 | Omura | 128/672 |

FOREIGN PATENT DOCUMENTS 3100610 7/1983 Fed. Rep. of Germany.

OTHER PUBLICATIONS

Linear Verstarker, Dr Ing. Gerd Harms.

Primary Examiner—William E. Wayner
Attorney, Agent, or Firm—Cushman, Darby & Cushman

[57] ABSTRACT

A measuring apparatus for the noninvasive determination of peripheral outflow and flow disturbances in the extremities of human beings includes at least one light transmitter for directing light onto the skin of the subject under test and at least one light receiver for receiving reflected radiation and an evaluation and read-out circuit for ascertaining the temporal course of the blood outflow or inflow in the veins by measuring the changes in light reflection. The evaluation and read-out circuit is provided with a digitally controlled tone generator and an electroacoustic transducer that emits a first signal to indicate readiness of the apparatus to effect measurement, a second succession of tones, the frequency of which follows the changes in the intensity of the light reflection until termination of the blood outflow or inflow, and a third signal which indicates the end of the measuring.

6 Claims, 5 Drawing Sheets

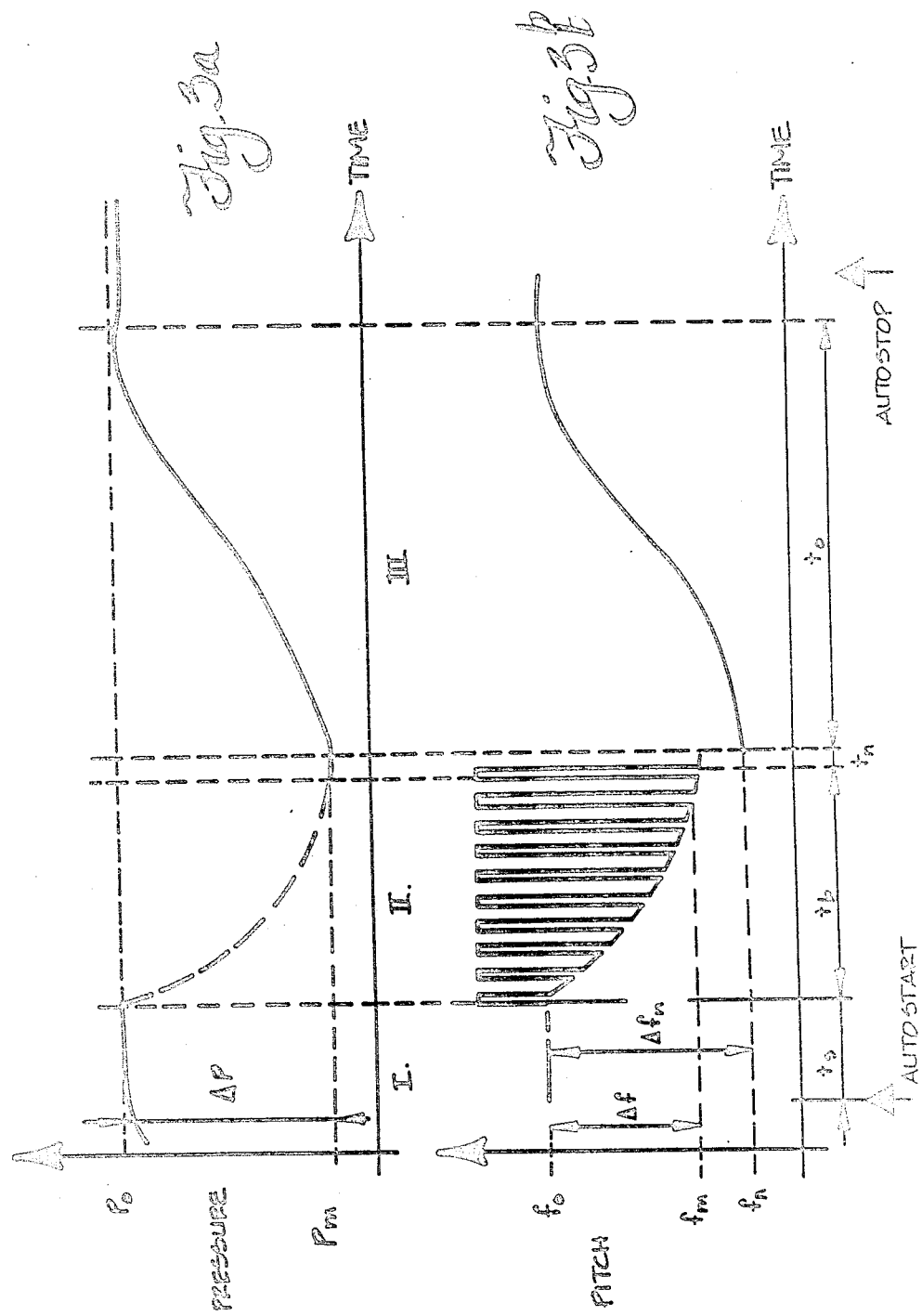

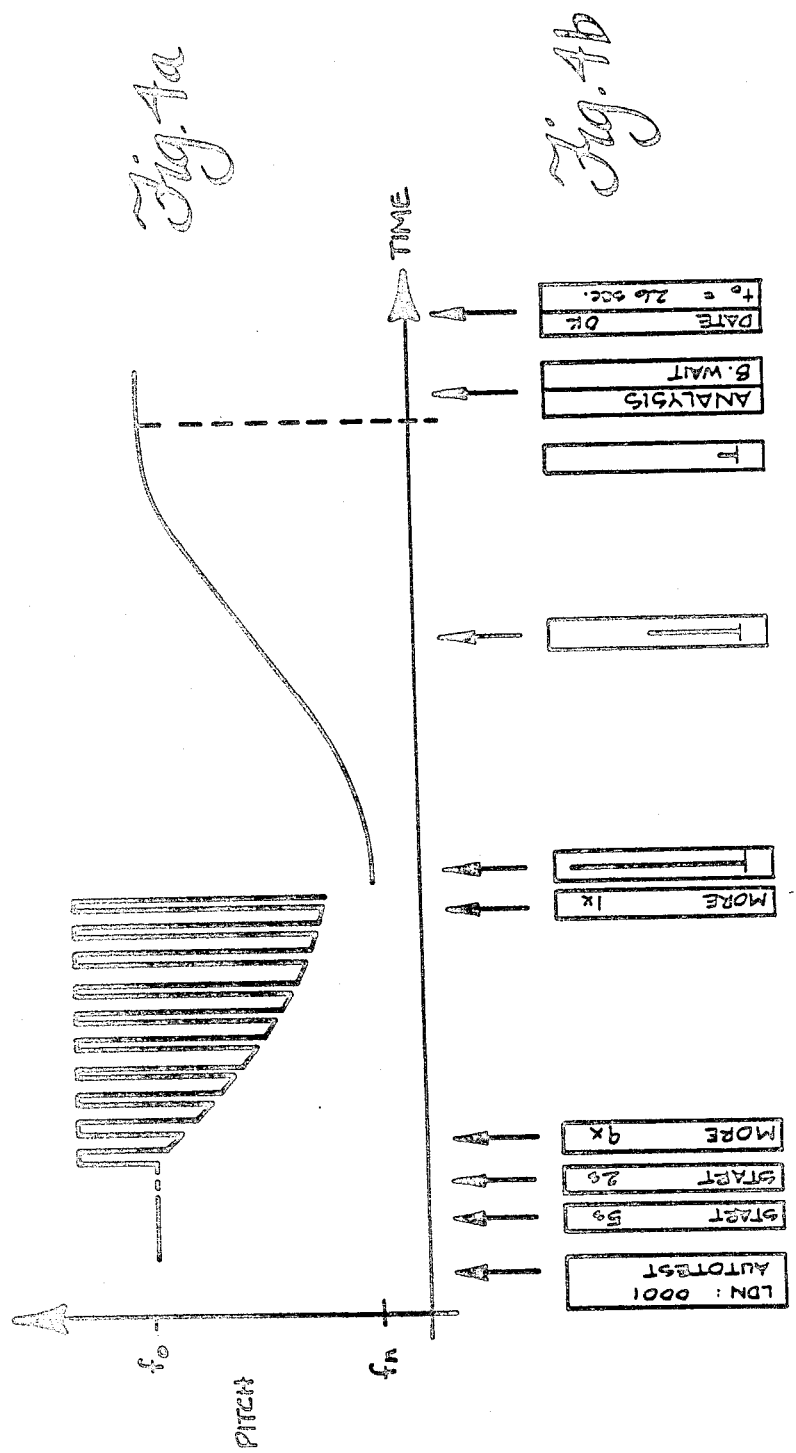

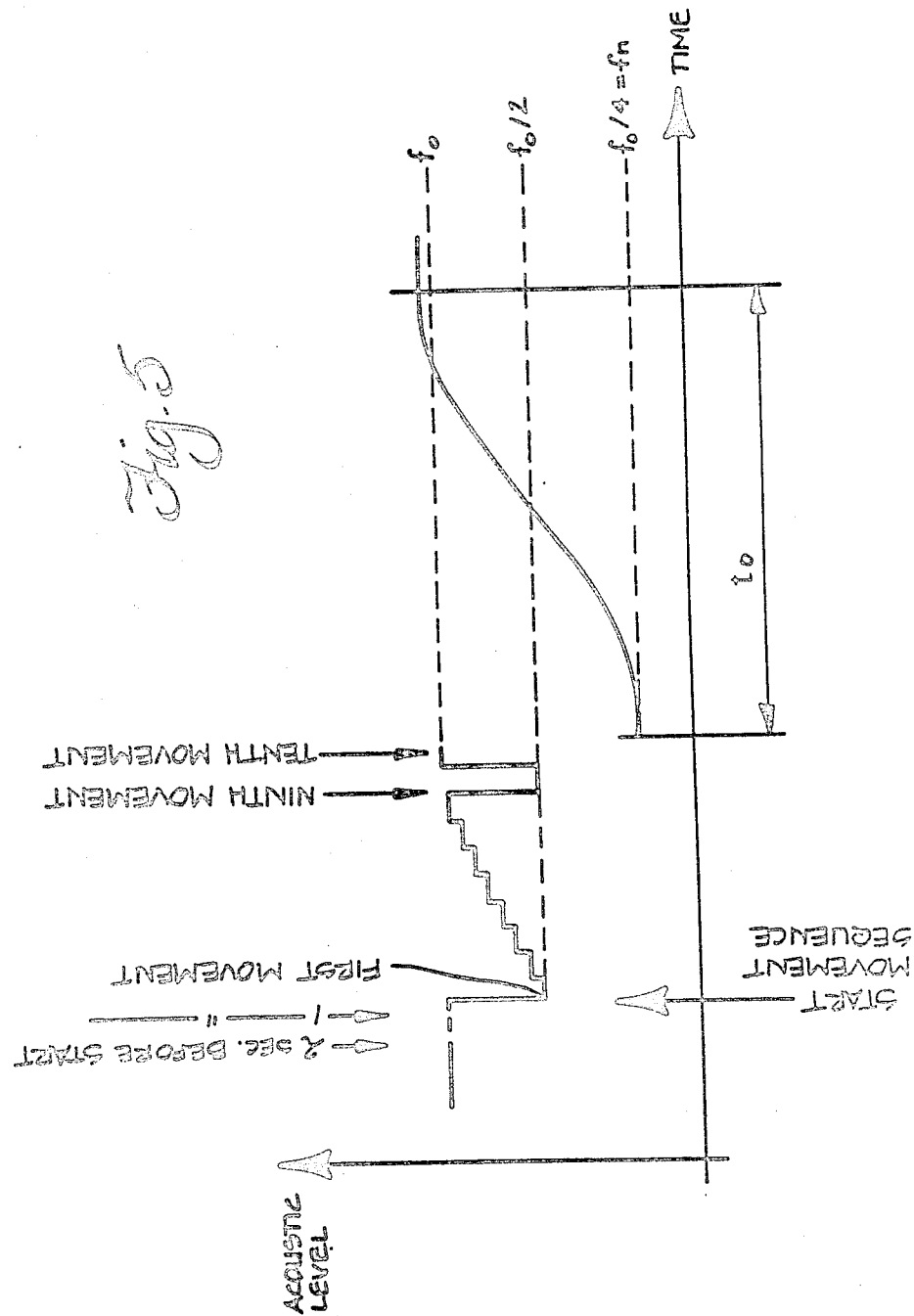

4,836,212

APPARATUS FOR THE NONINVASIVE DETERMINATION AND ACOUSTICAL REPRESENTATION OF THE DYNAMIC BEHAVIOR OF PERIPHERAL VENOUS HEMODYNAMIC

CROSS-REFERENCE TO RELATED APPLICATIONS

The subject matter of the present application is related to that disclosed in applicant's co-pending and commonly owned U.S. patent application Ser. No. 07/026,607, filed 3/17/87 and entitled "Microprocessor Controlled Apparatus for the Noninvasive Determination of Peripheral Outflow and Flow Disturbances," the disclosure of which is incorporated herein by reference.

BACKGROUND OF THE INVENTION

The present invention relates to a measuring apparatus for the noninvasive determination of peripheral blood outflow and flow disturbances in the extremities of human beings. Measuring devices of this type are disclosed in, by way of illustration, German Patent No. 31 00 610.8 or German Patent No. 33 18 746.0. In the measuring device disclosed in DE-PS No. 31 00 610.8, the temporal course of the reflected or dispersed back part of the radiation is evaluated in an analog manner and recorded by means of a recording device. In the measuring device disclosed in DE-PS No. 33 18 746.0, the analog signal is translated or converted into a digital signal by means of a transmission-reception data connection point circuit and transferred to a calculator device. The calculator device calculates the physical rating parameters for the analog light reflection curves. This measuring device is, accordingly, particularly suitable for conducting and evaluating a test series.

Both prior art measuring devices share the drawback that they cannot easily be constructed as handy, portable apparatuses: neither the recording device described in DE-PS No. 31 00 610.8 nor the common micro-computer with floppy disk drives, etc. described in DE-PS No. 33 18 746.0 can be miniaturized to the extent that they can be readily fabricated into a portable apparatus. Moreover, the power consumption of the prior art measuring devices is too great for portable apparatuses.

It is especially disadvantageous with regard to the prior art measuring devices that the operating staff determines the commencement and the termination of each measurement, thereby making subjective measurement errors possible.

SUMMARY OF THE INVENTION

In view of the above, it is an object of the present invention, among others, to provide a measuring apparatus for the noninvasive determination of peripheral outflow and flow disturbances in the extremities of human beings, which can also be constructed as a portable, hand-held apparatus.

The present invention is based on the fundamental idea that the evaluation circuit is provided with a digitally controlled tone generator and the read-out of the measuring results is provided by means of an electro-acoustic transducer. In this manner, it is possible to construct the measuring apparatus of the present invention as a compact and light-weight apparatus having low-power consumption requirements. The physician can easily carry the apparatus of the present invention around with him, by way of example, during an activity program in which physical exercises, etc. are performed and is able with little effort to examine the inflow or outflow of the veins immediately following the exercises, whereby the evaluation and read-out circuit emits a first signal which, by way of illustration, is an optical attention-attracting signal or, more preferably, an audible sound indicating to the examining individual that the apparatus is ready to measure and also provide a value representative of constant quiescent blood circulation of the skin. The actual measuring result, i.e., the measured light reflection is represented by a second succession of audible tones, the frequency of which follows the change in intensity of the light reflection, e.g., as a result of leg movements, until the blood outflow or inflow terminates. The end of the measurement, i.e., the return of a constant skin circulation following the executed movement, is indicated by a third signal, again preferably by a third audible tone or by a third succession of tones or even, for example, the end of the tone.

The acoustical read-out of the measuring results makes it possible for the examining individual to analyze the outflow or inflow of the veins or arteries and to detect abnormal changes, etc. with unexpected reliability.

It is, moreover, possible to use the tone generator and the electro-acoustic transducer, e.g., a loudspeaker, provided according to the invention, to support the activity program of the examining individual, by way of example, by means of a rhythmic succession of tones. Of course, it is possible to select from different successions of tones to support different activity programs.

The apparatus of the present invention can, by way of illustration, calibrate itself, whereby energy applied to the light transmitter or transmitters is continuously raised until the signal measured by the light receiver or receivers has attained a specific signal-to-noise interval. The first tone, indicating the commencement of readiness to measure, can then be emitted following termination of the self-calibration cycle.

The apparatus of the present invention can, of course, also be provided with a memory as well as a data output port. The measurement results can be stored in the memory and subsequently be transferred to another evaluation instrument. Naturally, it is also possible to transfer the measurement results and/or evaluation results during the measuring via a data line to another evaluation instrument, by way of illustration, a microcomputer or a printer.

The present invention provides a measuring apparatus for the noninvasive determination of peripheral outflow and flow disturbances in the extremities of human beings, having at least one light transmitter for directing light onto the skin of a human being and one light receiver for sensing light reflected therefrom as well as an evaluation and read-out circuit to ascertain the temporal course of the blood outflow or inflow in the veins by measuring the changes in light reflection. The invented apparatus distinguishes itself in that the evaluation and read-out circuit is provided with a digitally controlled tone generator and an electroacoustic transducer and emits a first signal to indicate readiness of the apparatus to effect measurement; a second succession of tones, the frequency of which follows the changes in the intensity of the light reflection until termination of the blood outflow or inflow; and a third signal which indicates the end of the measuring sequence.

Other objects and further scope of applicability of the present invention will become apparent from the detailed description to follow, taken in conjunction with the accompanying drawings, in which like parts are designated by like reference characters.

BRIEF DESCRIPTION OF THE DRAWING

FIGS. 3a and 3b illustrate a representation of the measurement results selected in accordance with the present invention;

FIGS. 4a and 4b illustrate the read-out of the acoustical representation of FIG. 3;

FIG. 5 illustrate an additional variation of the acoustical representation of FIGS. 4a and 4b.

DESCRIPTION OF THE PREFERRED EMBODIMENT

Figure 1:
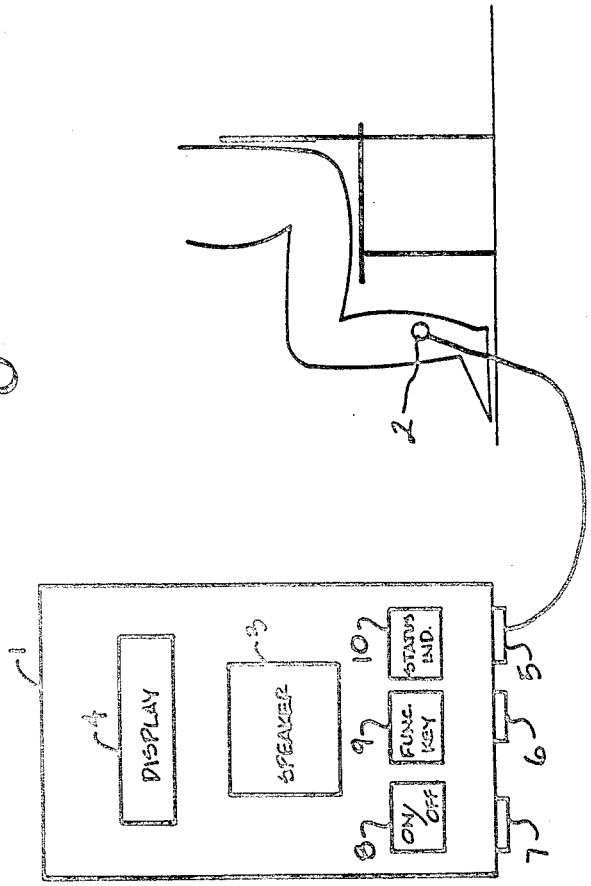
FIG. 1 illustrates an apparatus in accordance with the present invention in schematic form connected to a human subject.

As shown in schematic form in FIG. 1, a measuring apparatus 1 in accordance with the present invention is constructed as a small, portable apparatus. The measuring apparatus 1 is provided with an electro-acoustic transducer 3, by way of illustration, a loudspeaker, a LCD display unit 4, a plug 5 for an optical measuring head 2 having one or several light transmitters and receivers, which can be placed on the extremities of human beings, a plug 6 for earphones, as well as a plug 7 for connection to a stationary evaluation instrument to transfer data from the measuring apparatus 1. An on/off switch 8, a function key 9 for selecting the various operations, and an indicator key 10 (e.g., for the menu guide) are also provided.

Figure 2:
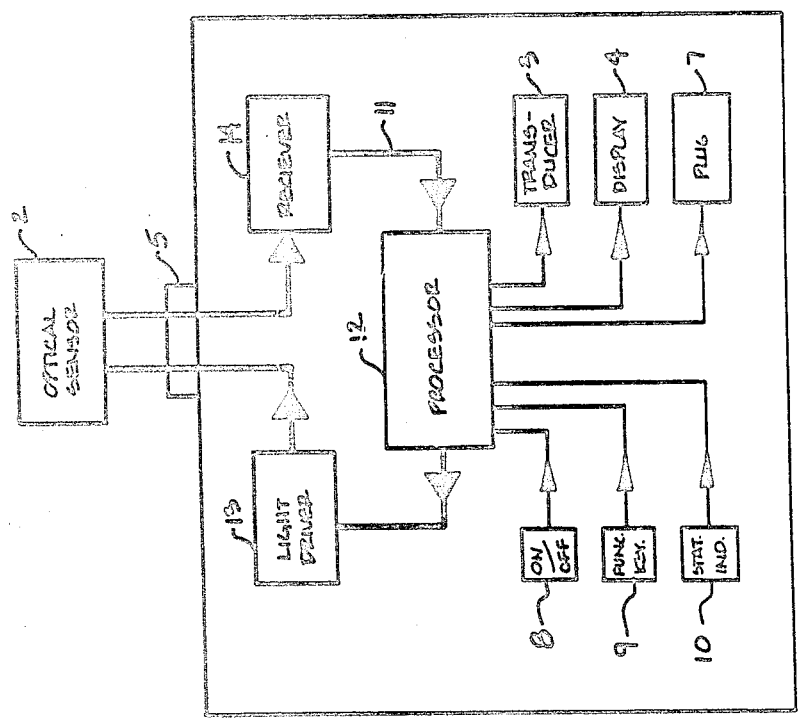
FIG. 2 depicts a block diagram of an evaluation and read-out circuit in accordance with the present invention.

FIG. 2 shows a block diagram of the evaluation and read-out circuit in accordance with the present invention, whereby the elements that are the same as in FIG. 1 are designated with the same reference characters. A microprocessor 12, a drive unit 13 for the light transmitter of the optical measuring head 2, and a receiver 14 for the light receiver of the optical measuring head 2 form an active control loop 11, whereby the drive unit 13 and the receiver 14 may be arranged in a manner similar to that disclosed in German Patent Nos. 31 00 610 and 33 18 746, the disclosures of which are incorporated herein by reference.

FIGS. 3 to 5 illustrate the mode of operation of the measuring apparatus 1 of FIGS. 1 and 2. FIG. 3a shows an example of a vein pressure curve, as it is obtained invasively by means of so-called phlebodynamometry. In phase I, a constant blood circulation of the skin is obtained from a seated patient and, as shown, is an almost constant pressure $P_o$. In phase II, the patient performs movements. Accordingly, the pressure drops from the value $P_o$ to the pressure $P_m$ characteristic of the respective state of the patient's blood vessels. Following termination of the activity or movement phase, the pressure rises again in phase III to approximately the initial value $P_o$. The time it takes for the pressure to rise again to the initial value $P_o$ is also an indication of the respective state of the patient's blood vessels.

As illustrated in detail, by way of example, in DE-PS No. 31 00 610, the light reflection detected by the optical detection head 2 follows the pressure curve illustrated in FIG. 3a.

FIG. 3b illustrates the acoustical read-out obtained with a measuring apparatus in accordance with the present invention using the pressure curve depicted in FIG. 3a. After the constant blood circulation in the skin of a seated patient is obtained and the self-calibration of the measuring apparatus 1 has been achieved, an audio tone with a frequency of $f_o$, for example, 1000 Hz., is emitted for a period of, by way of illustration, 10 seconds. Prior to the start of the first activity phase, the tone is briefly interrupted. These interruptions can be, by way of illustration, 1 or 2 seconds prior to the start of the first activity phase and are an indication to the examining individual that the activity program is beginning. In activity phase II, a tone is emitted during the time $t_b$ the frequency of which decreases corresponding to the drop in pressure from $P_o$ to $P_m$ from $f_o$ to $f_m$. Following termination of activity phase II, the frequency of the emitted tone is normed from the individual frequency $f_m$ for each person examined to a standard frequency $f_n$, whose value is, by way of illustration, 250 Hz ($f_o/4$). This frequency is preferred because the human ear is best able to differentiate changes in frequency in this frequency range.

During the inflow phase III, the frequency rises from the value $f_n$ to the initial value $f_o$. At the end of the inflow phase III, a tone of constant frequency is emitted during a period of, by way of illustration, 10 seconds. Subsequently measurement is terminated. Termination of measurement is indicated to the examining individual and preferably to the person being examined by the end of the tone.

Noninvasive measurement of dynamic behavior of peripheral venus hemodynamics takes place as described in German Pat. No. 3,100,610. In particular, the measurement device comprises a sensor which is placed on the skin of the subject in which a luminous diode serves as a light transmitter and a light receiver, e.g., a photo-sensitive dial. Reflected light is reflected by different layers of the subject's skin and received by the luminous diode. It is known in the art that the degree of reflection of light is correlated with emptying and filling of the veins, as described in German Pat. No. 3,100,610. According to the present invention, the emitted signal from the photo-sensitive diode is amplified and transposed, e.g., by means of a microcomputer, into a signal the frequency of which is within the sound frequency range of the acoustic spectrum.

FIG. 4b shows the reading on the LCD display unit 4 during measurement, corresponding to FIG. 3b, so that a more detailed description of FIG. 4a is not necessary. At the start of measuring, display unit 4 contains information indicating that self-calibration is being conducted at the time or how such time remains until the start of measuring. Subsequently, it indicates the number of tones still to be heard during the activity program and thereby the time remaining for the activity program. During the inflow phase it can, by way of illustration, display in a quasi analog manner the current skin reflection by the representation of a graph-like bar. Following termination of the inflow phase, the display unit 4 indicates, after a brief analysis period, e.g., the time required for the inflow. Switching to various other reading values ensues by means of the indicator key 10. In this manner, the display unit 4 supports, on the one hand, the acoustical result read-out, and can, on the other hand, be used for an interactive dialogue with the menu guide.

FIG. 5 shows another embodiment of the acoustical read-out of the measuring results in accordance with the present invention. In this embodiment, the person being examined is guided, during the activity phase, by the succession of tones emitted via the loudspeaker 3, whereby the tones can, by way of illustration, vary over an octave. The start of the inflow phase is indicated by the change in the tone by two octaves to lower frequencies, whereby the start tone $f_0$ preferably lies again at 1000 Hz. The inflow phase is again indicated by a change in pitch of the emitted tone.

Hereinbefore the present invention has been described in connection with preferred embodiments of the invention. Naturally, the most diverse modifications are possible within the scope of the inventive idea. By way of illustration, it is possible to guide the patient acoustically via the loudspeaker unit 3 while blood inflow or outflow is indicated to the examining individual by means of earphones. The frequency of the produced tones can, of course, also shift counter to the change in detected pressure. Furthermore, it is possible with the aid of the indicator key 10 to read-out other calculated parameters from the measured and stored measurement data following the termination of each measurement. With the aid of the function key 9 the following program packages can, by way of example, be selected from the program memory of the microcomputer 12: a standard measurement program, a data read-out program, and a learning and training program for the operating staff.

Thus it will be appreciated from the above that as a result of the present invention, a highly effective apparatus for the noninvasive determination and acoustical representation of the dynamic behavior of peripheral venous hemodynamic is provided by which the principal objective, among others, is completely fulfilled. It will be equally apparent and is contemplated that modification and/or changes may be made in the illustrated embodiment without departure from the invention. Accordingly, it is expressly intended that the foregoing description and accompanying drawings are illustrative of preferred embodiments only, not limiting, and that the true spirit and scope of the present invention will be determined by reference to the appended claims and their legal equivalent.

What is claimed is:

1. A measuring apparatus for the noninvasive determination of peripheral outflow and flow disturbances in the extremities of human beings, having at least one light transmitter and one light receiver as well as an evaluation and read-out unit to ascertain the temporal course of the outflow and inflow of blood in the veins by means of measuring the change in light reflection, whereby said evaluation and read-out circuit is provided with a digitally controlled tone generator and an electroacoustic transducer for emitting a first signal to indicate that the apparatus is ready to measure, a second succession of tones, the frequency of which follows the changes in the intensity of the light reflection until termination of blood outflow or inflow, and a third signal, which indicates the end of the measurement.

2. An apparatus according to claim 1, whereby the first and third signal are acoustic signals.

3. An apparatus according to claim 1, whereby the tone generator emits another succession of tones between the first tone and the second succession of tones to support an activity program.

4. An apparatus according to claim 1, whereby an additional succession of short impulses is integrated in the second succession of tones in order to improve the time information.

5. An apparatus according to claim 1, whereby said apparatus calibrates itself before commencing to measure and the tone generator emits the first tone after termination of said self-calibration.

6. An apparatus according to claim 1, whereby said apparatus is provided with a memory to store the measured results digitally.

* * * * *